(12) United States Patent
Hamatani et al.

(10) Patent No.: US 7,859,662 B2
(45) Date of Patent: Dec. 28, 2010

(54) ON-VEHICLE FUEL PROPERTY DETECTION DEVICE

(75) Inventors: Yutaro Hamatani, Tokyo (JP); Shigeki Kanamaru, Tokyo (JP); Tateki Mitani, Tokyo (JP); Eiji Yagyu, Tokyo (JP)

(73) Assignee: Mitsubishi Electric Corporation, Tokyo (JP)

( * ) Notice: Subject to any disclaimer, the term of this patent is extended or adjusted under 35 U.S.C. 154(b) by 378 days.

(21) Appl. No.: 11/856,959

(22) Filed: Sep. 18, 2007

(65) Prior Publication Data

US 2008/0204714 A1    Aug. 28, 2008

(30) Foreign Application Priority Data

Feb. 28, 2007 (JP) ............... 2007-049724

(51) Int. Cl.
*G01J 3/40* (2006.01)
(52) U.S. Cl. .................. 356/305; 356/72; 356/442; 385/12; 385/28; 385/123
(58) Field of Classification Search .................. 356/72, 356/442, 305; 385/12, 28, 123
See application file for complete search history.

(56) References Cited

U.S. PATENT DOCUMENTS 6,872,933 B2 * 3/2005 Wirthlin .................. 250/229
2009/0034901 A1 * 2/2009 Takabayashi et al. ......... 385/12

FOREIGN PATENT DOCUMENTS

JP    1-274042 A    11/1989
JP    2-236144 A    9/1990

* cited by examiner

*Primary Examiner*—Gregory J Toatley
*Assistant Examiner*—Iyabo S Alli
(74) *Attorney, Agent, or Firm*—Sughrue Mion, PLLC

(57) ABSTRACT

The detection device provides with an optical fiber composed of a core, a clad and a fiber jacket. A grating is applied to the core, and the fiber jacket located at the portion to which the grating is applied is removed so that the clad is in contact with a fuel fed to an injector of a vehicle. The detection device also provides with a light source for incidence of a light in a range of clad mode wavelength to the optical fiber, and a light-sensitive part for detecting an intensity of the light transmitting through the region to which the grating is applied. The optical fiber, light source and light-sensitive part are held in a conduit disposed in a fuel tank or between a fuel pump and the injector of the vehicle.

6 Claims, 4 Drawing Sheets

ON-VEHICLE FUEL PROPERTY DETECTION DEVICE

BACKGROUND OF THE INVENTION

1. Field of the Invention

The present invention relates to an on-vehicle fuel property detection device to be mounted on automobiles, motorcycles, etc. and, more particularly, to an on-vehicle fuel property detection device using an optical fiber sensor.

2. Description of the Related Art

It is a recent trend that alcohol-blended fuel mixed with bio-ethanol has been increasingly used in place of the conventional gasoline. In this alcohol-blended fuel, however, because of difference in optimum ignition timing, A/F and the like depending upon the contained-ethanol concentration, it is essential that alcohol concentration contained in the fuel is accurately detected in order to make appropriate control by engine control computer, i.e., ECU (electronic control unit).

To cope with this, it has been proposed that an alcohol-gasoline mixture ratio is measured with the use of an optical liquid sensor in which a large-caliber glass optical fiber provided with a light-emitting element at one end and a light-receiving element at the other end is folded back, and this folded part is exposed into a liquid to be measured coming in contact therewith to act as a detector part, as is disclosed, for example, in the Japanese Patent Publication (unexamined) 236144/1990 (ref. page 3, left upper col., lines 3 to 15; FIG. 1).

Further, it has been proposed that a fuel refractive-index detection side is formed on each of plural elongated light pipes in which a refractive index changes from a perimeter toward a core, and floodlighting object is prepared on one end face of the light pipe and a light-receiving object on the other end face, whereby an alcoholic content in a fuel is detected, as is disclosed, for example, in the Japanese Patent Publication (examined) 10654/1994 (ref. page 3, left col., lines 4 to 35; FIGS. 1 to 3).

In the mentioned conventional on-vehicle fuel property detection devices utilizing the optical fiber sensor, since a bent part is necessarily formed in the optical fiber, in order to suppress a bend loss in the propagated light intensity at this bent part, it is essential to secure a certain level of bend R, which has been a problem in downsizing the sensor itself. Moreover, it is a matter of course that use of plural light pipes (optical fibers) brings about a further problem in view of cost reduction and improvement in productivity due to complication of structure of the device itself.

SUMMARY OF THE INVENTION

The present invention was made to overcome the above-discussed problems. Before reaching a solution to the problems, the inventors came to have a following technical knowledge. That is, it is generally well-known in the optical communication system that, for the purpose of taking an optical signal of a specific wavelength propagating through an optical fiber transmission channel, a grating capable of reflecting a specific signal alone is employed. It is also well-known that, in the transmission characteristics of this grating, there exists a clad mode occurring at the time when the light propagating through inside the core reflects on or transmits through the grating. Since the clad mode brings about a loss ripple, the clad mode has been treated as unnecessary in the mentioned optical communication system. In this respect, as a result of researches, tests and evaluations, the inventors have found out that in the clad mode there is a difference in light intensity depending upon the refractive index of a material in contact with the outside of the clad (of which details are described in the Japanese Patent Application 2005-328622).

Accordingly, an object of the invention is to provide an on-vehicle fuel property detection device of small size and simple construction including an optical fiber sensor capable of measuring accurately an alcohol content in a fuel.

An on-vehicle fuel property detection device according to the invention includes: an optical fiber composed of a core, a clad and a fiber jacket, and in which a grating is applied to the mentioned core, and the mentioned fiber jacket located at the portion to which the mentioned grating is applied is removed so that the mentioned clad is in contact with a fuel fed to an injector of a vehicle; a light source for incidence of a light being in a range of clad mode wavelengths of the mentioned grating to the mentioned optical fiber; and a light-sensitive part for detecting an intensity of the light transmitting through the region to which the mentioned grating is applied. In this on-vehicle fuel property detection device, the mentioned optical fiber, light source and light-sensitive part are held in a conduit disposed in a fuel tank or between a fuel pump and the mentioned injector of the mentioned vehicle.

According to the invention, although an optical fiber type sensor is employed, not only an on-vehicle fuel property detection device of small size and simple construction can be obtained, but also this on-vehicle fuel property detection device is capable of measuring accurately an alcohol content in a fuel with the use of the optical fiber applied with the mentioned grating. Furthermore, the on-vehicle fuel property detection device can be provided at a reasonable cost, and there is no strict restriction in selecting a portion of any vehicle such as automobile, motorcycle where the on-vehicle fuel property detection device is mounted.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Embodiment 1

Figure 7:
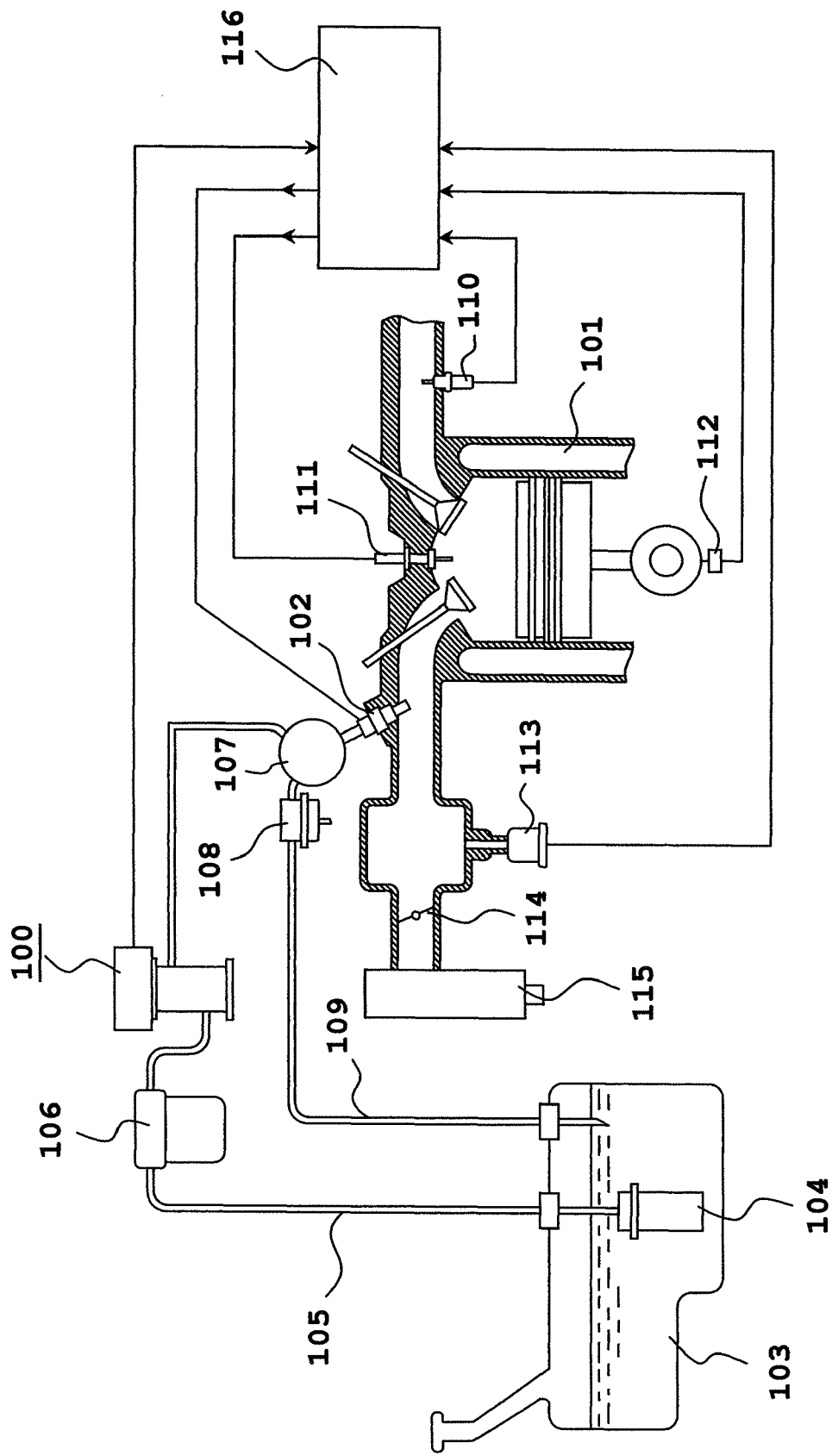
FIG. 7 is a schematic view showing an arrangement of a generally known on-vehicle fuel control system provided with a fuel property detection device 100.

With reference to FIG. 7 showing an arrangement of a generally known on-vehicle fuel control system provided with a fuel property detection device 100, first, construction and operation of a fuel control system as a whole are hereinafter described. In the drawing, reference numeral 101 denotes an engine of an automobile or the like, numeral 102 denotes a fuel injection valve, 103 denotes a fuel tank, numeral 104 denotes a fuel pump, numeral 106 denotes a high-pressure filter for filtering a fuel sucked up from the mentioned pump 104 via a fuel-feeding pipe 105, numeral 107 denotes a fuel distributor pipe, numeral 108 denotes a thermal pressure regulator, and numeral 109 denotes a fuel return pipe. Numeral 110 denotes an air-fuel sensor, numeral 111 denotes an ignition plug, numeral 112 denotes an engine speed sensor, numeral 113 denotes an intake pressure sensor, numeral 114 denotes a throttle valve, and numeral 115 denotes an air. Numeral 116 denotes a control unit consisting of an ECU. Signals from the fuel property detection device 100, signals from the air-fuel sensor 110, and signals from the engine speed sensor 112 and the intake pressure sensor 113, etc. are inputted to the control unit 116. This control unit 116 drives the fuel injection valve 102, the ignition plug 111, etc. based on a control variable corresponding to the input.

When feeding an alcohol-blended fuel to the fuel tank 103, the engine 101 is started, and at the same time, the alcohol-blended fuel is pressurized by the fuel pump 104. Then the alcohol-blended fuel is guided to the fuel property detection device 100 via the fuel-feeding pipe 105 and high-pressure filter 106, and alcohol content is measured there. The fuel is then flows in the distributor pipe 107, a part of the fuel is fed to the engine 101 through the fuel injection valve 102, and the other part is returned to the fuel tank 103 via the thermal pressure regulator 108 and fuel return pipe 109. The thermal pressure regulator 108 keeps the pressure up to the distributor pipe 107 constant at all times, irrespective of the consumption amount of the fuel injection valve 102. When the alcohol content measured by the fuel property detection device 100 is inputted to the control unit 116, this control unit 116 determines engine conditions based on signals of the engine speed sensor 112 and intake manifold pressure sensor 113, etc., and changes the fuel quantity fed to the engine by controlling the valve open time of the fuel injection valve 102. Then, air-fuel ratio is detected by the air-fuel ratio sensor 110 and is subject to a feedback control so that the air-fuel ratio comes to a target value conforming to the mentioned engine conditions. Ignition timing of the ignition coil 111 is also controlled conforming to the engine conditions.

Figure 1:
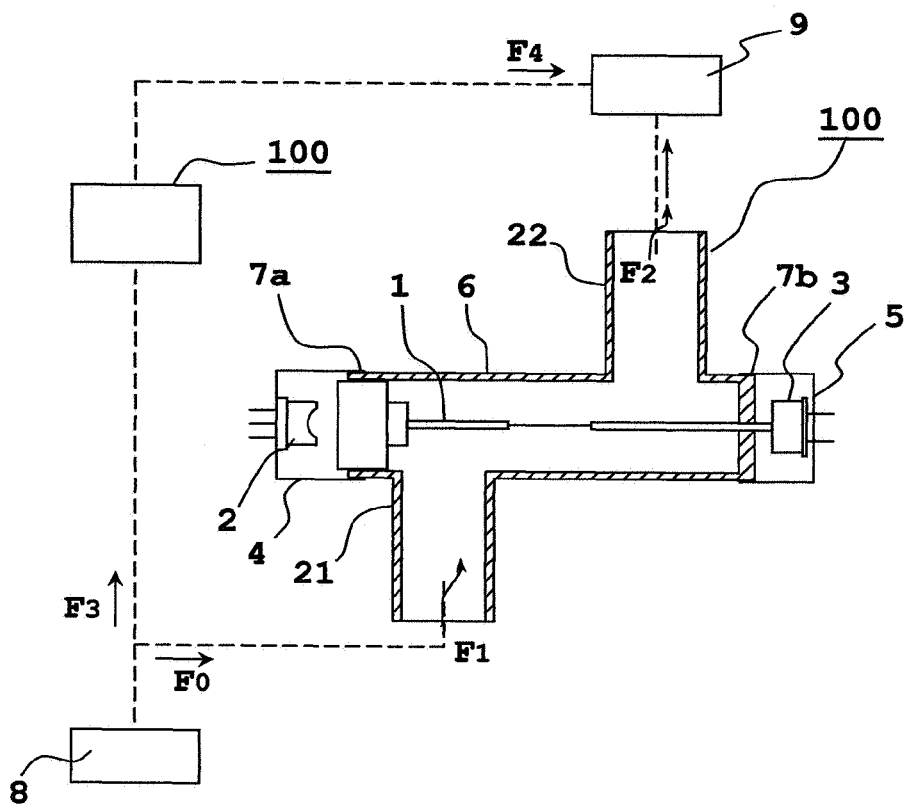
FIG. 1 is a schematic sectional view of an on-vehicle fuel property detection device 100 according to Embodiment 1 of the present invention.

Now, the on-vehicle fuel property detection device 100 according to Embodiment 1 is described. FIG. 1 is a schematic sectional view showing the on-vehicle fuel property detection device 100 according to Embodiment 1. In the drawing, reference numeral 1 denotes an optical fiber, numeral 2 denotes a light source consisting of a light-emitting element disposed on one end of the mentioned optical fiber 1, and numeral 3 denotes a light-sensitive part disposed on the other end. A light-emitting element such as light-emitting diode, laser diode can be employed as the light source 2, and a light-sensitive element such as spectrum analyzer, photodiode can be employed as the light-sensitive part 3. The light source 2 and the light-sensitive part 3 are mounted on a conduit 6 via holders 4, and 5 respectively. The optical fiber 1 is disposed in such a manner as passing through openings 7a and 7b provided in the conduit 6. In addition, the conduit 6 may be either directly connected to fuel conduit (fuel route) from a fuel tank 8 to an injector 9 through a fuel inlet 21 and a fuel outlet 22, as indicated by the arrows $F_0$, $F_1$ and $F_2$ or independently connected bypassing the mentioned fuel route as indicated by the arrows $F_3$ and $F_4$.

Figure 2:
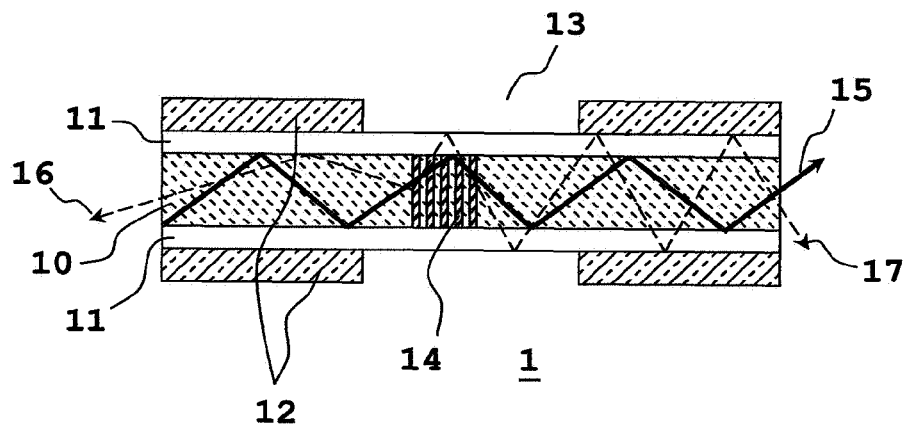
FIG. 2 is an explanatory view to explain propagation of light in an optical fiber of FIG. 1 and in clad mode.

FIG. 2 is an explanatory view to explain the principle of fuel property detection utilizing propagation of light, i.e., so called "clad mode", based on difference in refractive index on the periphery of the mentioned optical fiber 1. The optical fiber 1 consists of a core 10 where the light emitted from the light source 2 is propagated, a clad 11 covering the core 10 to enclose the light inside the core 10, and a fiber jacket 12 covering the clad 11 for protection. For the purpose of detecting the fuel properties in the periphery, a part of the fiber jacket 12 is removed so that the clad 11 is directly in contact with a fuel 13. Any inorganic glass such as quartz glass or any plastic material such as polymethylmethacrylate can be employed as the core 10 and the clad 11. Resins of fluorine, nylon, phenol, epoxy, melamine, and the like can be employed as the fiber jacket 12. In the detection of the fuel properties, it is utilized that intensity of a light referred to as "clad mode" produced at the time of reflection on or transmission through the grating 14 among the lights propagating through inside the core 10, is different depending on the refractive index of the fuel in contact with the outside of the clad 11. That is, in the part where no grating 14 is formed, the lights propagating through inside the core 10 run only through inside the core 10 repeating the reflection on the boundary face between in the core 10 and clad 11. When reaching the grating 14, the light is split into a light beam 15 transmitting through the grating 14 and propagating through inside the core 10, a light beam 16 being black-reflected on the grating 14 and propagating through inside the core 10 in the opposite direction, and a clad mode light beam 17 leaking out of the core 10 and propagating through inside the clad 11. Thus, an intensity of the light beam 15 transmitting through the grating 14 and propagating through inside the core 10 and that of the clad mode light beam 17 leaking out of the core 10 and propagating through inside the clad 11 can be detected by the light-sensitive part 3 of the optical fiber 1 located on the way of propagating direction of the light beams.

In this respect, wavelength characteristic of the intensity of light transmitted in the clad mode has a periodical peak of loss. Since the optical fiber 1 is immersed in the fuel 13, fluctuation range of the peak of loss varies depending on the refractive index of the fuel 13. Further, in the alcohol fuel, it is already known that the refractive index of the fuel is different depending on the ethanol content in the fuel. Accordingly, by detecting the variation in peak of loss in the transmission spectrum under the clad mode depending on the refractive index of the fuel, it becomes possible to estimate an alcohol concentration contained in the fuel based on the refractive index of the liquid.

Figure 3:
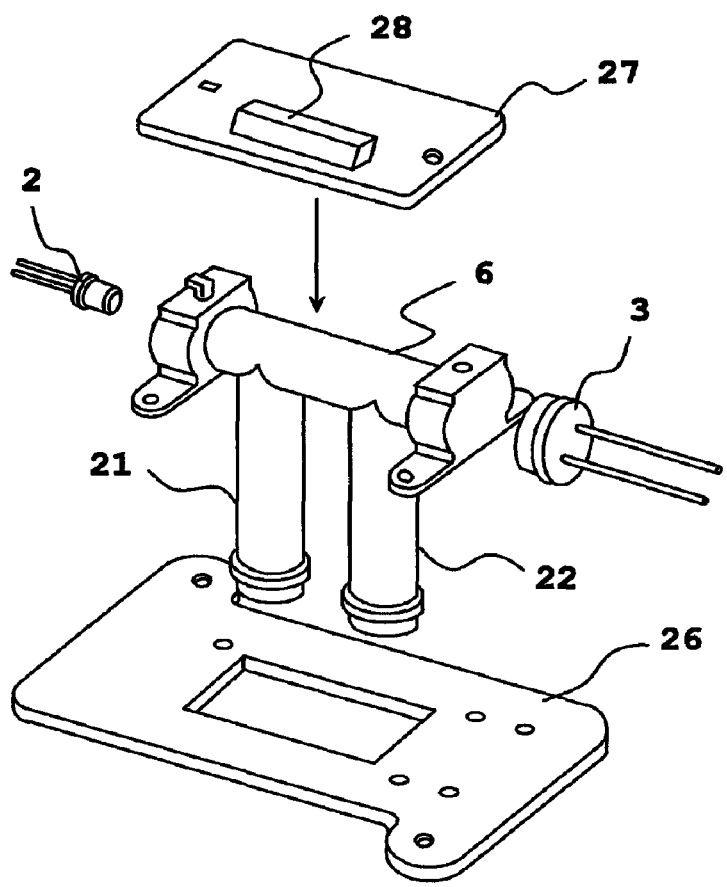
FIG. 3 is a perspective view showing the on-vehicle fuel property detection device 100 of FIG. 1 under installation.

Further to the above-described principle of detection, installation of the on-vehicle fuel property detection device 100 on a vehicle is now described with reference to FIG. 3. In this installation, the conduit 6 is directly connected into the fuel tank. That is, as indicated by the arrows $F_0$, $F_1$ and $F_2$, the conduit 6 is directly connected to the fuel conduit (fuel route) from the fuel tank 8 to the injector 9 through the fuel inlet 21 and the fuel outlet 22.

The conduit 6 is fitted to any place of a vehicle not illustrated via a bracket 26 formed by resin molding, forging or sheet metal working. In this case, it is preferable that the fuel inlet 21 and the fuel outlet 22 are provided on the conduit 6 in the same direction and on the side opposite to a drive circuit board 27 to which the light source 2 or the light-sensitive part 3 is connected via a lead wire not illustrated.

As a result of providing the fuel inlet 21 and the fuel outlet 22 in the same direction, not only the drive circuit board 27 and the bracket 26 can be designed more freely, but also it becomes possible to make the installation without interfering with assembly work each other with respect to the light source 2, light-sensitive part 3, fuel inlet 21 or fuel outlet 22. Furthermore, the drive circuit board 27 is provided with a connector 28 to connect the light source 2 or the light-sensitive part 3 to an outside power supply not illustrated and further to the ECU. Also in this case, since the fuel inlet 21 and the fuel outlet 22 are provided in the same direction and on the side opposite to the drive circuit board 27, a signal wire from the connector 28 can be led at a right angle with respect to the conduit 6, resulting in improvement in assembly work efficiency.

In this manner, the fuel properties can be detected sufficiently on condition that the grating area acting as a sensor is a few millimeters in length. In combination with the mentioned fitting method of the sensor part, even in the case of using an optical fiber, the conduit or the detection device itself can be down-sized.

Embodiment 2

Figure 4:
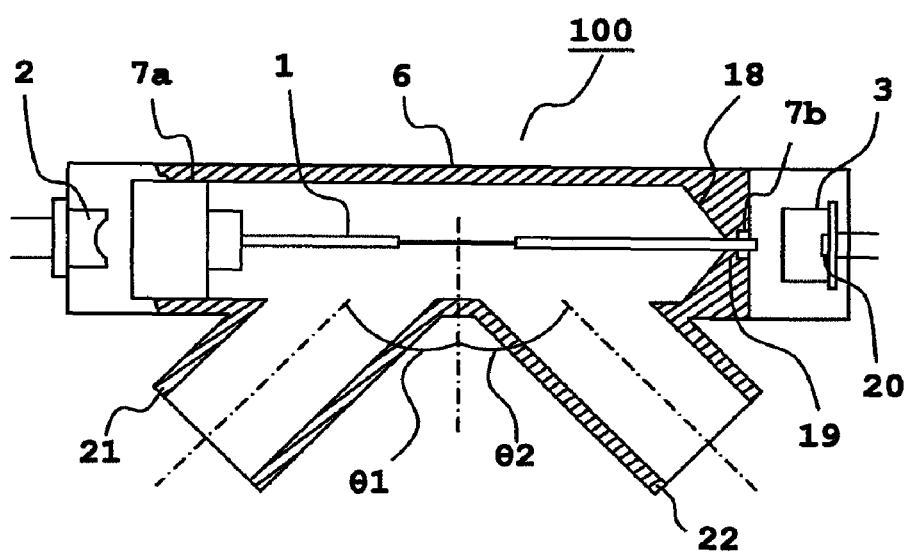
FIG. 4 is a schematic sectional view of an on-vehicle fuel property detection device 100 according to Embodiments 2 and 3 of the invention.

FIG. 4 is a schematic sectional view of an on-vehicle fuel property detection device 100 according to Embodiment 2 of the invention, and is relevant to FIG. 1 showing Embodiment 1. In the foregoing Embodiment 1, as shown in FIG. 3, the fuel inlet 21 and fuel outlet 22 are each formed into a conduit through which a fuel flows in or out vertically. On the other hand, in this Embodiment 2, the fuel inlet 21 and fuel outlet 22 are designed each with a gradient with respect to the optical fiber 1. Accordingly, the fuel flown from the fuel inlet 21 into the conduit 6 reaches the optical fiber 1 at an arbitrary angle θ1. Thereafter, the fuel having reached the optical fiber 1 is discharged from the fuel outlet 22 at an arbitrary angle θ2. Consequently, as compared with the foregoing Embodiment 1, a fuel drag on the optical fiber 1 at the time of start up or at the time of pulsation in fuel flow can be relaxed.

Embodiment 3

With reference to FIG. 4, an improvement of the opening 7b is described as Embodiment 3. The optical fiber 1 is disposed so as to pass through the opening 7b provided in the conduit 6. In such a construction, when the opening 7b is formed in substantially the same dimensions as the internal diameter of the conduit 6 like the opening 7a, it will be a very easy work to provide the optical fiber 1 through inside. However, from the viewpoint of air-tightness of the on-vehicle fuel property detection device 100 itself or consistency (that is, alignment) with the light-sensitive part 3, the mentioned construction forming the opening 7b in substantially the same dimension as the internal diameter of the conduit 6 is not always advantageous. In the case of forming the opening 7b in such a manner that the external diameter of the optical fiber 1 is in contact with the opening 7b, it is certain that air-tightness and consistency are improved, but it will be difficult to provide the optical fiber 1 through inside. To overcome this, in this Embodiment 3, the opening 7b is tapered, i.e., provided with a taper 18. Thus, the optical fiber 1 inserted from the opening 7a reaches the taper 18 through the conduit 6. At this time, since the taper 18 guides the optical fiber 1, it is easy for the optical fiber to reach the opening 7b. Furthermore, the optical fiber 1 guided by the taper 18 can reach nearly the center of the light-sensitive element 20 of the light-sensitive part 3 passing through a straight region 19 provided in the conduit 6 and having a diameter suited to a contour of the optical fiber 1.

Accordingly, according to this Embodiment, not only the air-tightness and consistency is improved but also the working efficiency in laying the optical fiber through inside the conduit is improved. In particular, positioning of the light-sensitive part 3 with respect to the optical fiber 1 is not required, and assembling accurately is easy. As a result, the irregularity in performance of the detection device due to assembly work can be reduced as much as possible.

Embodiment 4

Figure 5:
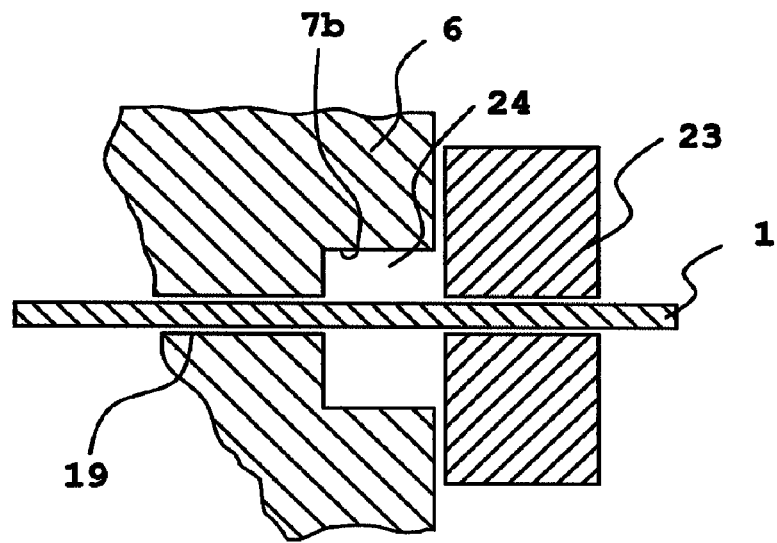
FIG. 5 is a sectional view showing in detail an example of sealing an opening of an on-vehicle fuel property detection device 100 according to Embodiment 4 of the invention.

Air-tightness is discussed in the foregoing Embodiment 3. In view of balancing the air-tightness with the installation of the optical fiber through inside the conduit, it is required that the optical fiber 1 has a certain clearance at the straight region 19 (see FIG. 4). Accordingly, it is necessary to seal the optical fiber 1 having passed through the straight region with any sealing member. In this Embodiment 4, application of such a seal is described in detail with reference to FIGS. 5 and 6. In an example shown in FIG. 5, the opening 7b provided on the conduit 6 is sealed with a low-melting glass to keep the air-tightness inside the conduit 6, after having passed the optical fiber 1 therethrough. This low-melting glass is applied to the optical fiber 1 having passed through the opening 7b in such a manner that the optical fiber 1 is inserted through a ring or saddle-shaped low-melting glass preform 23. Further, the opening 7b located on the conduit 6 is provided with a counter bore 24 of which diameter is smaller than the contour of the low-melting glass preform 23 for sealing. In this manner, at the time of melting the low-melting glass preform 23, it becomes easy for the molten glass to flow in the internal part of the bore (straight region 19), thereby securing abroad sealing area, resulting in a desirable sealing performance.

Figure 6:
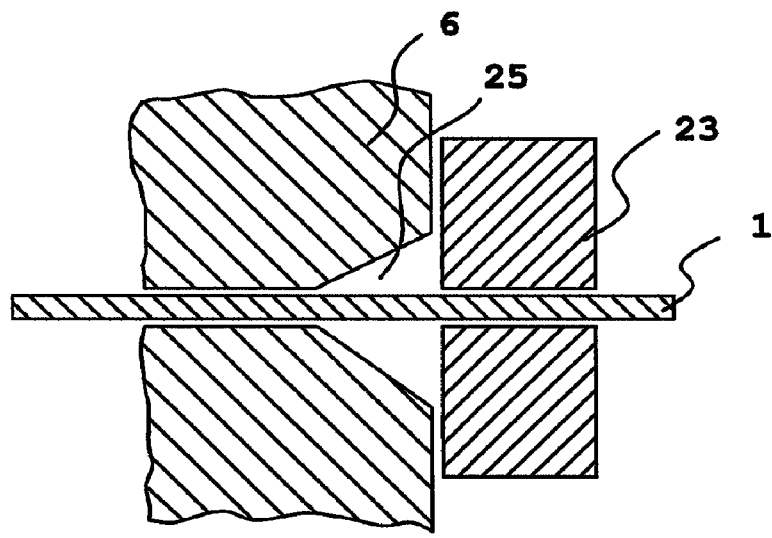
FIG. 6 is a sectional view showing in detail another example of sealing an opening of the on-vehicle fuel property detection device 100.

In another example shown in FIG. 6, the opening 7b located on the conduit 6 is provided with a tapered bore 25 of which diameter is smaller than the contour of the low-melting glass preform 23 in place of the mentioned counter bore 23. As a result, it becomes easier for the molten glass to flow in the internal part of the tapered bore 25.

While the presently preferred embodiments of the present invention have been shown and described, it is to be understood that these disclosures are for the purpose of illustration and that various changes and modifications may be made without departing from the scope of the invention as set forth in the appended claims.

What is claimed is:

1. An on-vehicle fuel property detection device comprising:
   a conduit disposed in a fuel tank or between a fuel pump and said injector of the vehicle;
   an optical fiber disposed inside the conduit and composed of a core in a part of which a grating is applied, a clad covering the core, and a fiber jacket covering the clad in which a portion corresponding to the part which said grating is applied is removed so that said clad is in contact with a fuel fed to an injector of a vehicle;
   a light source disposed on one end of the conduit and entering a light being in a range of clad mode wavelengths of said grating to said optical fiber; and
   a light-sensitive part disposed on the other end of the conduit and detecting an intensity of the light transmitting through the region to which said grating is applied;
   wherein said conduit is provided with a fuel inlet and a fuel outlet, each are open in the direction different from an axial direction of the conduit.

2. The on-vehicle fuel property detection device according to claim 1, wherein said fuel inlet and fuel outlet are open in the same direction.

3. The on-vehicle fuel property detection device according to claim 2, wherein the fuel inlet and the fuel outlet are open to have a gradient with respect to the optical fiber.

4. The on-vehicle fuel property detection device according to claim 2, wherein signal wires from the light source and the light-sensitive part are led at a right angle with respect to the fuel inlet and the fuel outlet.

5. The on-vehicle fuel property detection device according to claim 1, wherein the conduit is provided with a through hole at said other end for passing the optical fiber through and is tapered between the through hole and internal diameter part of said conduit.

6. The on-vehicle fuel property detection device according to claim 5, wherein the optical fiber passing through the through hole is sealed with a low-melting glass on the outside of the conduit.

* * * * *